(12) United States Patent
McDaniel et al.

(10) Patent No.: US 7,264,778 B2
(45) Date of Patent: Sep. 4, 2007

(54) CARBON MONOXIDE SENSOR AND METHOD OF USE THEREOF

(75) Inventors: Anthony H. McDaniel, Livermore, CA (US); J. Will Medlin, Boulder, CO (US); Robert J. Bastasz, Livermore, CA (US)

(73) Assignee: Sandia Corporation, Livermore, CA (US)

(*) Notice: Subject to any disclaimer, the term of this patent is extended or adjusted under 35 U.S.C. 154(b) by 720 days.

(21) Appl. No.: 10/387,921

(22) Filed: Mar. 12, 2003

(65) Prior Publication Data

US 2004/0178082 A1 Sep. 16, 2004

(51) Int. Cl.
*B32B 5/02* (2006.01)
*B32B 27/04* (2006.01)
*B32B 27/12* (2006.01)
*G01N 27/00* (2006.01)
*H01L 21/00* (2006.01)

(52) U.S. Cl. .................. 422/98; 422/83; 436/134; 436/149; 438/48; 438/49; 438/142; 29/592.1; 257/213; 257/252; 257/253

(58) Field of Classification Search .......... 422/83, 422/98; 436/134, 149; 438/48, 49, 142; 29/592.1; 257/213, 252, 253
See application file for complete search history.

(56) References Cited

U.S. PATENT DOCUMENTS

| | | | | |
|---|---|---|---|---|
| 4,058,368 A | | 11/1977 | Svensson et al. ......... 23/254 E |
| 4,324,760 A | | 4/1982 | Harris .................... 422/98 |
| 4,514,263 A | * | 4/1985 | Janata ..................... 205/782 |
| 4,613,422 A | * | 9/1986 | Lauks ..................... 204/419 |
| 5,250,171 A | | 10/1993 | Warburton et al. ......... 204/431 |
| 5,279,795 A | * | 1/1994 | Hughes et al. ............. 422/98 |
| 5,367,283 A | | 11/1994 | Lauf et al. ................ 338/34 |
| 5,417,821 A | * | 5/1995 | Pyke ..................... 205/775 |
| 5,439,580 A | | 8/1995 | Akbar et al. ............. 204/425 |
| 5,576,067 A | | 11/1996 | Miyayama et al. ....... 427/443.2 |
| 5,650,054 A | | 7/1997 | Shen et al. ............... 204/412 |
| 5,897,766 A | | 4/1999 | Kawatsu ................. 204/426 |
| 6,001,499 A | | 12/1999 | Grot et al. ............... 429/22 |
| 6,041,643 A | * | 3/2000 | Stokes et al. ............. 73/31.06 |
| 6,254,749 B1 | | 7/2001 | Yokota et al. ............ 204/424 |
| 6,293,137 B1 | | 9/2001 | Liu et al. ................ 73/31.06 |
| 6,316,133 B1 | | 11/2001 | Bossel .................... 429/17 |
| 6,368,479 B1 | | 4/2002 | Yokota et al. ............ 204/424 |
| 6,429,019 B1 | | 8/2002 | Goldstein et al. .......... 436/134 |
| 2006/0196246 A1 | * | 9/2006 | Li et al. .................... 73/23.2 |

OTHER PUBLICATIONS

Tracy, J. C.; Palmberg, P. W.: "Structural Influences on Adsorbate Binding Energy. I. Carbon Monoxide on (100) Palladium," *The Journal of Chemical Physics*, V.51, pp. 4852-4862 (1969).

(Continued)

*Primary Examiner*—Brian Sines
(74) *Attorney, Agent, or Firm*—Reed & Associates

(57) ABSTRACT

Carbon monoxide sensors suitable for use in hydrogen feed streams and methods of use thereof are disclosed. The sensors are palladium metal/insulator/semiconductor (Pd-MIS) sensors which may possess a gate metal layer having uniform, Type 1, or non-uniform, Type 2, film morphology. Type 1 sensors display an increased sensor response in the presence of carbon monoxide while Type 2 sensors display a decreased response to carbon monoxide. The methods and sensors disclosed herein are particularly suitable for use in proton exchange membrane fuel cells (PEMFCs).

26 Claims, 5 Drawing Sheets

OTHER PUBLICATIONS

Conrad, H.; Ertl, G.; Koch, J.; Latta, E. E.; "Adsorption of CO on Pd Single Crystal Surfaces," *Surface Science 43*, pp. 462-480 (1974).

Bradshaw, A. M.; Hoffmann, F. M.; "The Chemisorption of Carbon Monoxide on Palladium Single Crystal Surfaces: IR Spectroscopic Evidence for Localised Site Adsorption," *Surface Science 72*, pp. 513-535 (1978).

Lundstrom, I.; "Hydrogen Sensitive MOS-Structures Part I: Principles and Applications," *Sensors and Actuators*, 1, pp. 403-426 (1981).

Lundstrom, I.; Soderberg, D.; "Hydrogen Sensitive MOS-Structures Part 2: Characterization," *Sensors and Actuators 2*, pp. 105-138 (1981/82).

Kok, G. A.; Noordermeer, A.; Nieuwenhuys, B. E.; "Decomposition of Methanol and the Interaction of Coadsorbed Hydrogen and Carbon Monoxide on a Pd(111) Surface," *Surface Science 135*, pp. 65-80 (1983).

Noordermeer, A.; Kok, G. A.; Nieuwenhuys, B. E.; "A Comparative Study of the Behaviour of the PdAg(111) and Pd(111) Surfaces Towards the Interaction with Hydrogen and Carbon Monoxide," *Surface Science 165*, pp. 375-392 (1986).

Bastasz, R.; Hughes, R. C.; "Hydrogen particle diagnostic based on Pd-MOS diode arrays," *Rev. Sci.Instrum.* 59, pp. 184-186 (1988).

Ratajczykowa, I.; "The Influence of CO on Hydrogen Sorption by Pd(111) Single Crystals," *Surface Science 172*, pp. 691-714 (1986).

Hughes, R. C.; Bastasz, R.; "Low-energy proton detection by Pd metal-insulator-semiconductor diodes," *Journal of Applied Physics 64*, pp. 6839-6844 (1988).

Hughes, R. C.; Taylor, P. A.; Ricco, A. J., Rye, R. R.; "Kinetics of Hydrogen Adsorption and Absorption: Catalytic Gate MIS Gas Sensors on Silicon," *Journal of Electrochemical Soc.*, V. 136, No. 9, pp. 2653-2661 (1989).

Fogelberg, J.; Petersson, L.-G.; "Kinetic modelling of the $H_2$-$O_2$ reaction on Pd and of its influence on the hydrogen response of a hydrogen sensitive Pd metal-oxide-semiconductor device," *Surface Science 350*, pp. 91-102 (1996).

Eriksson, M.; Ekedahl, L.-G.; "The influence of CO on the response of hydrogen sensitive Pd-MOS devices," *Sensors and Actuators B42*, pp. 217-223 (1997).

Johansson, M.; Lundstrom, I.; Ekedahl, L.-G.; "Bridging the pressure gap for palladium metal-insulator-semiconductor hydrogen sensors in oxygen containing environments," *Journal of Applied Physics*, v.84, No. 1, pp. 44-51 (1998).

Eriksson, M.; Ekedahl, L.-G.; "Real time measurements of hydrogen desorption and absorption during CO exposures of Pd: hydrogen sticking and dissolution," *Applied Surface Science*, pp. 89-97 (1998).

Eriksson, M.; Ekedahl, L.-G.;"The catalytic oxidation of CO on polycrystalline Pd: experiments and kinetic molding," *Surface Science 412/413*, pp. 430-440 (1998).

Hara, S.; Sakaki, K.; Itoh, N.; "Decline in Hydrogen Permeation Due to Concentration Polarization and CO Hindrance in a Palladium Membrane Reactor," *Ind. Eng. Chem. Res.*, pp. 4913-4918 (1999).

Amandusson, H.; Ekedahl, L.-G.; Dannetun, H.; "The effect of CO and $O_2$ on hydrogen permeation through a palladium membrane," *Applied Surface Science 153*, pp. 259-267 (2000).

Monnier, J. R.; Medlin, J. W.; Kuo, Y.-J.; "Selective isomerization of 2,5-dihydrofuran to 2,3-dihydrofuran using CO-modified, supported Pd catalysts," *Applied Catalysis A: General*, pp. 463-474 (2000).

Pyke, S. C.; Sadwick, L.; "Gallium Nitride Integrated Gas/Temperature Sensors for Fuel Cell System Monitoring for Hydrogen and Carbon Monoxide," *Proceedings of the 2002 U. S. DOE Hydrogen Program Review*, pp. 1-11 (2000).

Medlin, J.W.; McDaniel, A.H.;Allendorf, M.D.; Bastasz, R.: "Effects of competitive carbon monoxide adsorption on the hydrogen response of metal-insulator-semiconductor sensors: the role of metal film morphology," *Journal of Applied Physics* v.93(4), pp. 2267-2274, Feb. 15, 2003.

\* cited by examiner

CARBON MONOXIDE SENSOR AND METHOD OF USE THEREOF

ACKNOWLEDGEMENT OF GOVERNMENT SUPPORT

The United States Government has rights in this invention pursuant to Contract No. DE-AC04-94AL85000 between the United States Department of Energy and Sandia Corporation for the operation of Sandia National Laboratories.

TECHNICAL FIELD

The present invention relates to the field of chemical sensors, particularly to the field of carbon monoxide sensors for use in proton exchange membrane fuel cells.

BACKGROUND OF THE INVENTION

Proton exchange membrane fuel cells (PEMFC) are an attractive alternative for converting chemical energy to electrical energy. Given the expanding availability of hydrogen from alternative sources, PEMFC technology promises to reduce the dependence of the U.S. economy on foreign oil. Domestic primary fuel resources, i.e., natural gas, alcohols, and petroleum distillates, may be converted to hydrogen through steam reforming, water-gas shift, and partial oxidation processes. These secondary hydrogen sources are attractive, at least in the near term, as significant infrastructure exists within the U.S. for the processing and distribution of these primary fuels. Current PEMFC technologies are, however, extremely sensitive to trace levels of contaminants that exist within the aforementioned fuels, such as hydrogen sulfide, often found in natural gas, and carbon monoxide, a byproduct of all fuel-conversion processes.

Clearly, detection and removal of undesired contaminants in PEMFC fuel streams is a major technological challenge. Transition metals such as platinum and ruthenium make up the catalytically-active portion of the membrane in a PEMFC and the catalytic activity of these metals is susceptible to reduced functionality or permanent deactivation (poisoning) by carbon monoxide and sulfur. Cell voltage, current flux, and membrane life decrease dramatically at part-per-million levels (5-100 ppm) of carbon monoxide and PEMFC catalysts are even less tolerant to sulfur in the form of $H_2S$ or mercaptan. Considerable efforts are, therefore, underway to design more tolerant membrane structures, as well as advanced fuel pre-conditioners (located post-reformer) that can reduce carbon monoxide and sulfur concentrations to acceptable levels via reaction, separation, or a combination of both.

Chemical sensors play an important role in managing carbon monoxide and sulfur in a PEMFC unit by providing information on contaminant levels within the cell stack and fuel processors. In addition, feedback from chemical sensors is a necessary input to closed-loop control and process optimization strategies. While the need for carbon monoxide and sulfur detection within the PEMFC environment is well established, the availability of process-compatible devices is lacking. Sensing technologies based on wet or dry electrochemical cells are currently limited by choice of ionic conductor and lack of chemical specificity.

For example, detecting carbon monoxide in gases using solid state devices (dry cells) has matured to the point of commercialization (e.g., home carbon monoxide monitors). These types of sensors are based on supported metal-oxide semiconductors (SMOS). One key component to such devices is the availability of oxygen in the sensing environment to convert carbon monoxide to carbon dioxide. Essentially, oxygen atoms are removed from the surface via catalytic oxidation of carbon monoxide, which induces an oxygen ion gradient within the sensor that is detectible as a small electrical current passing through the ionic conductor. The concentration of oxygen in a reformats stream and/or fuel feed to a cell stack is quite limited thereby rendering SMOS sensors completely ineffective without elaborate sample preparation/handling schemes. Other known carbon monoxide sensor types involve a wet electrochemical cell and are equally challenging in a PEMFC system.

The development of carbon monoxide sensors for use in PEMFC systems is further complicated by the presence of other gases in the fuel stream that could potentially interfere with a reliable measurement. For example, incomplete steam reforming of methanol produces residual quantities of formic acid, formaldehyde, and methyl formate, in addition to un-reacted methanol. Imparting intrinsic chemical selectivity to SMOS sensors is currently an active field of research with incremental gains targeted towards niche applications. In principle, hydrogen, as well as any of the aforementioned compounds resulting from methanol reforming, can be oxidized by the sensor and thereby hinder an accurate determination of the carbon monoxide and/or sulfur content in the matrix. The same would be true for residual hydrocarbons resulting from incomplete processing of natural gas or petroleum distillate.

Another method for detecting carbon monoxide in PEMFC essentially involves creation of a mini-PEM and locating it within the sensing environment. There here are a number of difficulties associated with this technique, such as increased noble metal loading needed to attain the necessary sensitivity, given that the mini-PEM has a reduced surface area. In addition, oxygen must still be part of the sensing system if electrical measurements are to be obtained Hydrogen sensors based on metal-insulator-semiconductor (MIS) technology have been in existence for more than two decades. Due to their extreme sensitivity to hydrogen, they have been used as leak detectors to assure safety in the work place. Currently, MIS sensors have only been used in limited applications. This is due to the fact that the surface chemistry by which these sensors operate can be strongly affected by parasitic reactions and deactivation by catalyst poisons which result in cross-sensitivities to analytes other than hydrogen and which may reduce or extinguish sensor performance. While the increased sensitivity of these sensors is undesirable for industrial process monitors, this sensitivity renders them well suited for monitoring fouling agents in the PEMFC environment. MIS sensors with catalytic metal gates of palladium (Pd) are devices with proven capabilities to detect sub-ppm quantities of hydrogen in relatively inert atmospheres. It is well known that Pd-MIS structures, such as capacitors, field effect transistors, and tunneling diodes, saturate at low partial pressures of hydrogen (less than 1% at 1 atmosphere), and therefore can not function as a hydrogen sensor in a PEMFC system. The use of such Pd-MIS sensors in the detection of carbon monoxide is, however, unknown.

SUMMARY OF THE INVENTION

In one embodiment of the invention, a carbon monoxide sensor suitable for use in a hydrogen feed stream is provided. The carbon monoxide sensor is comprised of a metal/insulator/semiconductor structure capable of generating electrical signals in response to hydrogen and carbon monoxide, and means for processing the electrical signals to determine if carbon monoxide is present in the hydrogen feed stream. The metal/insulator/semiconductor structure may take the form of a capacitor, a field effect transistor, or a diode and may be formed of a semiconductive substrate, an insulating inorganic oxide layer on the substrate, a gate metal layer deposited on the insulating inorganic oxide layer, and first and second conductor means respectively connected to the gate metal layer and the substrate.

The gate metal layer is a palladium or palladium alloy and is approximately 20 nm to approximately 500 nm in thickness. The gate metal layer may posses a non-uniform film morphology defined by variations in the thickness of the gate metal layer that are greater than approximately 10 nm. The non-uniform film morphology may take the form of a plurality of pits or cavities in the gate metal layer that may optionally expose the silicon dioxide layer. Generally these pits or cavities cover approximately 1% to approximately 30% of the gate metal layer. If desired, a selectively permeable membrane comprised of an organic material such as a sol gel or an inorganic material such as a zeolite may be placed on the surface of the gate metal layer.

In another embodiment of the invention, a method is provided for determining the presence of carbon monoxide in a hydrogen feed stream of interest. In the method, a carbon monoxide sensor, as described above, is first provided. A calibration signal is then also provided. The calibration signal indicates the sensors response to a hydrogen feed stream that is free of carbon monoxide. The sensor is then exposed to the feed stream of interest and the electrical signals generated by the sensor are recorded. The initial signals generated by the sensor during exposure to the hydrogen feed stream of interest may be used to derive the calibration signal or the signal may be otherwise obtained from exposure of the sensor to a carbon monoxide-free hydrogen feed stream. The presence of carbon monoxide in the hydrogen feed stream of interest is determined by comparing the calibration signal to the signals generated by the sensor when exposed to the hydrogen feed stream of interest.

When a sensor is used that possesses a gate metal layer having a non-uniform film morphology, the calibration signal will be greater than the signals generated when carbon monoxide is present. Conversely when a sensor is used that possesses a uniform film morphology, the calibration signal will be less than the signals generated when carbon monoxide is present. The method of the visit of the invention is capable of detecting carbon monoxide concentrations ranging from approximately 0.05 ppm to approximately 1000 ppm at atmospheric pressure and can be carried out a temperature ranging from approximately 80° C. to approximately 250° C.

Additional objects, advantages, and novel features of the invention will be set forth in part in the description that follows, and in part will become apparent to those skilled in the art upon examination of the following, or may be learned by practice of the invention.

BRIEF DESCRIPTION OF THE DRAWINGS

FIG. 2A is an image of a gate metal layer having a smooth film morphology while FIG. 2B is an image of a gate metal layer having a non-uniform film morphology.

FIG. 5A shows the response to a fuel stream having $P_{H2}$=500 mTorr, $P_{CO}$=850 mTorr. FIG. 5B shows the response when the sensor is exposed to a fuel stream having $P_{H2}$=75 mTorr, $P_{CO}$=37 mTorr. In each figure, the mass spectrometer signal for $H_2$ and CO in the flow cell is also shown in order to indicate the exposure sequence and the rate of analyte accumulation.

DETAILED DESCRIPTION OF THE INVENTION

Figure 1:
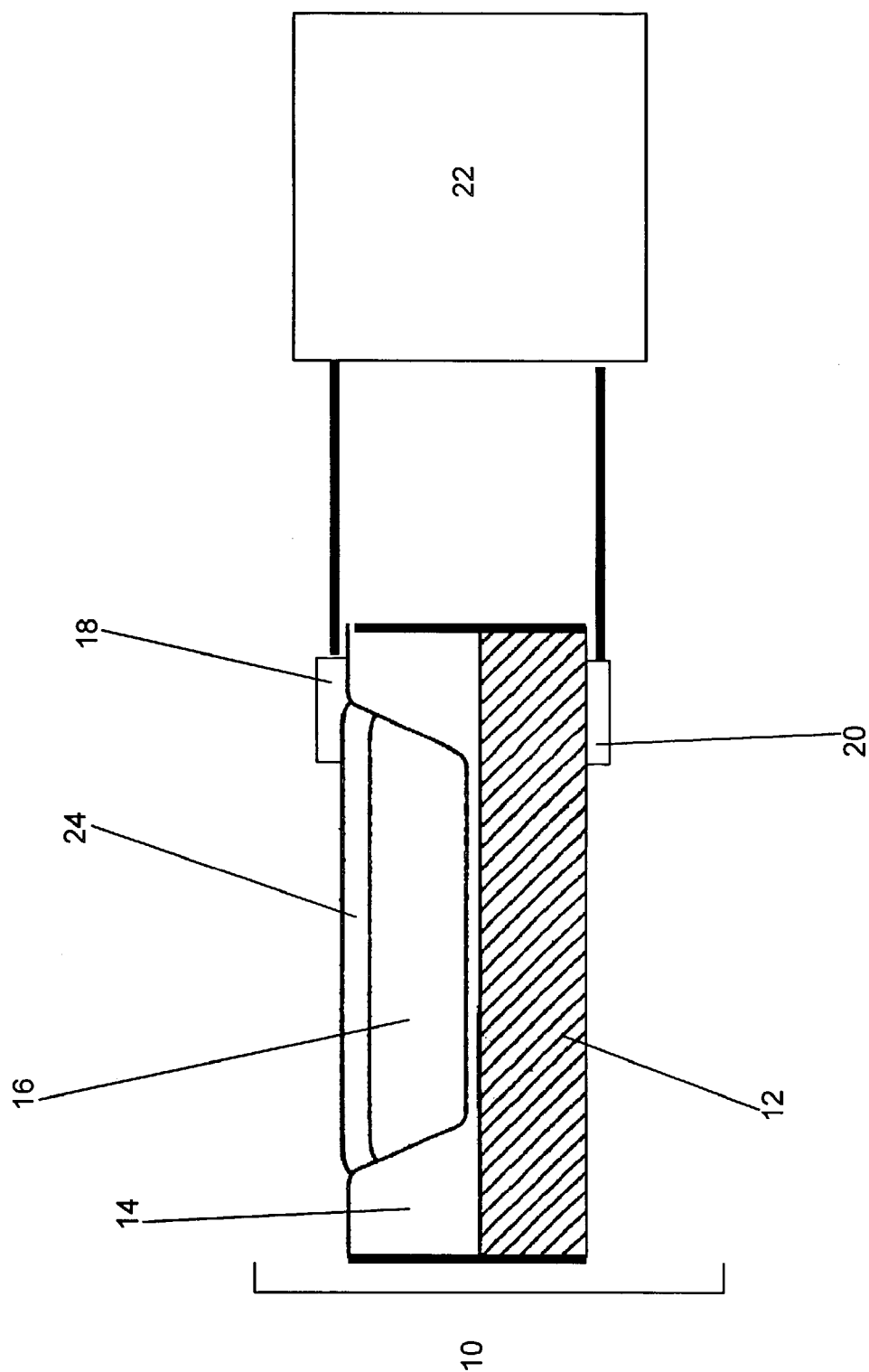
FIG. 1 is an illustration of a cross sectional view of a sensor of the invention.

Overview and Definitions:

Before describing the present invention in detail, it is to be understood that unless otherwise indicated this invention is not limited to specific sensor materials or manufacturing processes, as such may vary. It is also to be understood that the terminology used herein is for the purpose of describing particular embodiments only, and is not intended to be limiting.

It must be noted that, as used herein, the singular forms "a," "an," and "the" include plural referents unless the context clearly dictates otherwise. Thus, for example, "a sensor" encompasses not only a single sensor but also two or more sensors, and the like.

MIS devices that utilize an active catalyst as the gate metal have been demonstrated to be sensitive to hydrogen gas, and devices that incorporate Pd as metal components are particularly responsive. The basic mechanism by which these devices function is well-known. In brief, gaseous hydrogen dissociatively adsorbs on the Pd surface, liberating surface hydrogen atoms. The hydrogen atoms can then defuse rapidly through the bulk of the Pd surface to the Pd—$SiO_2$ interface, where they are trapped at interfacial sites. This interfacial atomic hydrogen alters the Shottky barrier of the MIS structure, resulting in a shift of the capacitance-voltage (C-V) curve for a capacitor or the current-voltage (I-V) curve for transistor. And because all steps in this process are reversible and the concentration of interfacial hydrogen varies measurably over a wide range of hydrogen pressures, these MIS structures can continuously monitor fluctuations in hydrogen levels.

Although adsorption of carbon monoxide on Pd surface is known, the effect of this phenomenon on MIS devices has not been extensively studied. Eriksson et al. (1997) *Sensors and Actuators B*, 42:217-223 reported that under ultrahigh vacuum (UHV) conditions, variation in the C-V curve for a carbon monoxide/hydrogen mix was negligible compared to the C-V response for exposure to hydrogen gas alone. Thus, Pd-MIS sensors were not found to be responsive to carbon monoxide. The present invention is based on the surprising discovery that the aforementioned Pd-MIS hydrogen sensors can be used as carbon monoxide sensors in higher pressure, hydrogen-rich environments encountered in PEMFC applications.

The Carbon Monoxide Sensor:

As discussed above, the carbon monoxide sensor of the invention is comprised of a metal/insulator/semiconductor structure capable of generating electrical signals in response to hydrogen and carbon monoxide, and means for processing the electrical signals to determine if carbon monoxide is present in the hydrogen feed stream of interest. The metal/insulator/semiconductor (MIS) structure may be any conventionally used semiconductor structure that possesses a gate-metal-layer and is capable of generating signals in response to the presence of hydrogen and carbon monoxide. Examples of such MIS structures include, but are not limited to, field effect transistors (FET), tunneling diodes, and capacitors. Although the present invention is described herein as having capacitor MIS structures, it must be emphasized that a wide variety of MIS structures are suitable for use in the present sensor. Other suitable MIS structures include FET devices such as metal-ferroelectric-semiconductor FET ("MFS-FET"), diodes such as tunneling diodes, and the like. Such structures are well known and will be readily understood by those skilled in the art.

FIG. 1 depicts a simple embodiment of the invention wherein the metal/insulator/semiconductor structure takes the form of a capacitor 10 which is comprised of a semiconductive substrate 12, an insulating inorganic oxide layer 14 on top of the semiconductive substrate 12, a gate metal layer 16 formed by depositing a metal layer on top of a thinned region of the insulating inorganic oxide layer 14, and first and second conductor means 18 and 20 respectively connected to the gate metal layer 16 and the semiconductive substrate 12. Attached to the first and second conductor means 18 and 20 is the means for processing the electrical signals 22, which will usually take the form of an integrated circuit. FIG. 1 also depicts an optional selectively permeable membrane 24 which overlays gate metal layer 16. This selectively permeable membrane will be discussed in greater detail below.

The semiconductive substrate is typically formed of Si, Ge, GaP, InAs, InP, SiGe, GaAs or other III/V compounds. Of the aforementioned materials, silicon and similar semiconductive materials such as an n-doped silicon wafer are preferred. The insulating inorganic oxide layer is typically a layer of silicon dioxide, although other semiconductor devices such as tunneling diodes and field-effect devices which incorporate the same catalytic gate metal (palladium), but have very different underling semiconductor structures that may or may not incorporate $SiO_2$. Suitable inorganic oxide layers for these types of MIS structures are well known in the art and will be readily available to anyone of ordinary skill in the art. The inorganic oxide layer ranges in thickness from approximately 1 nm to approximately 20 nm, with thicknesses ranging from approximately 2 nm to approximately 10 nm being more common.

The gate metal layer is comprised of palladium or a palladium alloy. It will be appreciated by those of skill in the art that palladium can be alloyed with a variety of other metals including, but not limited to, silver, gold, copper, nickel, and platinum. The metal selected to form the palladium alloy will impact on the crystal structure of the gate metal layer, e.g., expanding or contracting the structure. Alloys having contracted crystal structures, such as palladium/nickel alloys, will possess a higher tolerance to hydrogen while alloys having an expanded crystal structure, such as palladium/gold alloys, will have increased sensitivity to carbon monoxide. Alloys of palladium and gold and palladium and nickel are particularly preferred. Typically, the gate metal layer ranges in thickness from approximately 20 nm to approximately 500 nm. Thicknesses ranging from approximately 20 nm to approximately 200 nm are more common.

In one embodiment of the invention, the surface of the gate metal layer has a uniform film morphology while in a second embodiment, the gate metal layer has a non-uniform film morphology. Sensors having uniform film morphologies, hereinafter Type 1 sensors, are characterized by a smooth, even gate metal layer covering the insulating inorganic oxide layer. In contrast, sensors having non-uniform film morphologies, hereinafter Type 2 sensors, are characterized by variations in the thickness of the gate metal layer that are greater than approximately 10 nm. The variations in the thickness of the gate metal layer may take the form of a plurality of pits or cavities in the gate metal layer that may optionally expose the insulating inorganic oxide layer. In Type 2 sensors, the pits or cavities cover approximately 1% to approximately 30% of the gate metal layer.

It has been surprisingly discovered that the morphology of the gate metal film plays a significant role in the way in which the sensor responds to the presence of carbon monoxide in the hydrogen feed stream. When sensors having uniform film morphologies are used, i.e., when Type 1 sensors are used, the presence of carbon monoxide in the hydrogen feed stream results in an increase in the hydrogen signal. In contrast, when Type 2 sensors are used, the introduction of carbon monoxide into the feed stream produces a decrease in the sensor response.

While not wishing to be bound by theory, it is believed that the varying effects of the gate metal film morphology are due to the carbon monoxide "trapping" the hydrogen atoms in the interfacial layer. In sensors having a uniform film morphology, carbon monoxide preferentially adsorbs on the surface of Pd metal and blocks the pathways by which hydrogen adsorbs and diffuses in the metal layer, thereby "trapping" the hydrogen in the interfacial layer and resulting in an increase in the sensor response. In Type 2 sensors, it is believed that the pits and cavities provide pathways that enable the escape of the otherwise "trapped" hydrogen while limiting the further adsorption of hydrogen on the surface of the sensor and, thereby, resulting in a decrease in the sensor response.

The first and second conductive means may be any conventionally known electrode system and the fabrication and design of such electrical connections will be well known and understood by those of skill in the art. The means for processing the electrical signals generated by the MIS structure to indicate the presence of carbon monoxide will involve a comparison of the currently generated signal to a known calibration signal and will usually be performed via microcircuitry of either analog or digital design.

The calibration signal may be based on either a sensor response to a hydrogen feed stream that is free of carbon monoxide or may be derived from the initial sensor response, e.g., within the first 10 seconds of exposure of the sensor to the hydrogen feed stream of interest. As hydrogen interacts more quickly with the Pd surface than does carbon monoxide, readings taken within the first few seconds of exposure to the feed stream reflect only the presence of hydrogen. Any variation in the signal output between the calibration signal and the currently generated signal will indicate the presence of carbon monoxide in the hydrogen feed stream.

The calibration signal may also be obtained via a reference sensor but, as the levels of hydrogen present in fuel feeds in PEMFC systems range in the area of approximately 35-100 mol percent, the carbon monoxide sensors will be saturated with respect to the hydrogen-dependant signal and, therefore, a reference electrode will not be required. When it is anticipated that the sensor will be saturated with respect to the hydrogen dependent signal, the calibration signal will be determined by the upper limit of the sensor response. Under these conditions, Type 2 sensors are favored as the presence of carbon monoxide results in a clearly observable decrease in the sensor response.

If desired, the carbon monoxide sensor may also comprise a selectively permeable membrane that covers the gate metal layer. Such a membrane is shown in FIG. 1 as layer 24. The selectively permeable membrane may be used to better control the exposure of the hydrogen feed stream to the catalytic surface of the sensor and to induce or augment chemical selectivity to fouling agents. Suitable selectively permeable membranes include, but are not limited to organic polymer membranes and inorganic oxides or zeolites, and zeolite membranes are particularly preferred. Such selectively permeable membranes are well known within the art.

As stated above, it is preferred that the selectively permeable membrane be an inorganic oxide zeolite. This is due to the fact that crystalline frameworks within zeolites have "tunable" pores that are capable of size exclusion separations. In contrast, organic polymer membranes are based on diffusion separations, not size exclusion, and do not have the inherent thermal and mechanical stability of inorganic films. Also, zeolite membranes may be modified with desired catalytic elements that chemically liberate hydrogen from analytes and thereby impart increased functionality to the sensor.

Sensor Fabrication:

The carbon monoxide sensors of the invention may be fabricated using known techniques. Generally, the insulating inorganic oxide layer is formed on the surface of the semiconductive substrate by thermal oxidation or other coating processes. The gate metal layer may be prepared using a variety of deposition and post-deposition methods. For thermal evaporation and sputtering of the active metal, substrate temperature and deposition rate will impact grain size and therefore influence film characteristics. If a sensor having a non-uniform film morphology is desired, electroplating techniques, including pulse plating, straight plating and reverse current plating, may also be used to create highly dendritic micro-textures in the film. Post-deposition ion milling and/or wet chemical etching may also be used to roughen the metal surface.

Traditional approaches toward synthesis of thin film membranes comprising zeolites generally fall into three main classes. Self-supporting membranes can be made, essentially using sintering techniques. Alternately, it is possible to grow single crystal zeolite films on suitable substrates. The most intensively pursued approach toward fabricating thin film membranes which comprise active zeolites is to grow defective zeolite films (usually polycrystalline in structure), and attempt to fill in the defects using secondary growth of zeolites atop the original layer, or by depositing carbonaceous material in the defects. Other suitable methods for forming a selectively permeable zeolite membrane are disclosed in U.S. Pat. No. 6,494,326 to Nenoff, et al.

Use in Carbon Monoxide Detection:

The carbon monoxide sensors of the invention are designed for the detection of carbon monoxide in hydrogen feed streams and are particularly well suited for use in PEMFC systems. In the method of the invention, the sensor, as described above, is placed into contact with the hydrogen feed stream of interest. A calibration signal, derived either from the initial sensor reading or from a separate exposure to a carbon monoxide-free feed stream, is used as a comparison value for detection of carbon monoxide. As discussed above, if a Type 1 sensor is used, the presence of carbon monoxide will be indicated by an increase in the hydrogen response of the sensor. In cases where a Type 2 sensor is used, carbon monoxide will be indicated by a decrease in sensor response.

It should be noted that the method of the invention is quite sensitive to the presence of carbon monoxide as the hydrogen response of the Pd-MIS sensors of the invention is dramatically altered by even small amounts of carbon monoxide (<20 ppm). Thus, the method of the invention is capable of detecting carbon monoxide at concentrations ranging from approximately 0.05 ppm to approximately 1000 ppm at atmospheric pressures. The magnitude of the carbon monoxide-induced attenuation is temperature dependent, allowing for carbon monoxide sensitivity to be tuned with thermal regulation. Generally, the method is carried out at a temperature ranging from approximately 80° C. to approximately 250° C.

It is to be understood that while the invention has been described in conjunction with the preferred specific embodiments thereof, the foregoing description and the examples that follow are intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

Experimental

The following examples are put forth so as to provide those of ordinary skill in the art with a complete disclosure and description of how to prepare and use the compositions disclosed and claimed herein. Efforts have been made to ensure accuracy with respect to numbers (e.g., amounts, temperatures, rates, times, etc.) but some errors and deviations should be accounted for. Unless indicated otherwise, parts are parts by weight, temperature is in degrees Celsius (° C.), and pressure is at or near atmospheric. Additionally, all starting materials were obtained commercially or synthesized using known procedures.

EXAMPLE 1

Sensor Fabrication

A silicon substrate was first cleaned in a solution of 200 mls $H_2SO_4$ and 85 ml $H_2O_{2s}$. After rinsing, the substrate was dipped for 10 seconds in a solution of 200 ml $H_2O$ and 20 ml HF and then rinsed again. The cleaned substrate was then air dried and oxidized for 420 minutes at 1050° C. to provide a thick layer of oxidized material, approximately 5000 Å in thickness.

Next, the oxide layer was removed from the back of the substrate and from selected regions of the upper surface using a standard 4330 photoresist developed in MF319. The patterned substrate was then oxidized for an additional 45 minutes to provide a thin layer of oxidation at the bottom of the patterned areas.

Once patterned and oxidized, the substrate was placed in a thermal evaporator and a gate metal layer of Pd, approximately 200 nm thick, was deposited over the entire upper surface of the substrate. In order to remove the gate metal coating from undesired areas of the substrate, i.e., from the unpatterned areas, a 5214 image reversal process with metal mask was used. The substrate was spin coated with photoresist at 5000 rpm and baked at 110° C. for 45 seconds. A metal mask was used to protect the areas where the palladium layer was to remain. The photoresist layer was then flood exposed for 45 seconds and the exposed photoresist developed in MF312 1:1.4 for 45-60 seconds.

After the unpatterned areas of the metal layer were exposed, the metal was removed via sputtering. The substrate was connected to the stage in the sputtering area using thermal paste in order to minimize heat effects that might damage the photoresist protecting the patterned areas. Typically, removal of the palladium layer took approximately 1 minute 15 seconds. The photoresist layer was then removed using acetone.

Metallic bond pads were then selectively deposited on the surface of the gate metal layer. A 9245 photoresist coating was placed on the upper surface of the substrate and patterned. After removal of the patterned areas of photoresist, 80 Å of Cr and 3000 Å of Au were deposited onto the patterned areas via thermal evaporation. Once deposition of the Cr and Au was complete, the remaining photo resist was removed using acetone. The upper surface of the metallic coated substrate was the protectively coated with 4330 photoresist.

Any remaining oxide was removed from the bottom of the substrate via etching and the bottom surface then coated with a 80 Å Cr and 3000 Å Au layer. The bottom of the substrate was then also protectively coated with 4330 photoresist and the substrate was cut into individual capacitors, each pattered area forming one capacitor. The individual capacitors were approximately 0.5 $cm^2$ in area. Once separated, the capacitors were washed with acetone, methanol, and isopropanol to remove the protective photoresist coating and then dried.

Figure 2A:
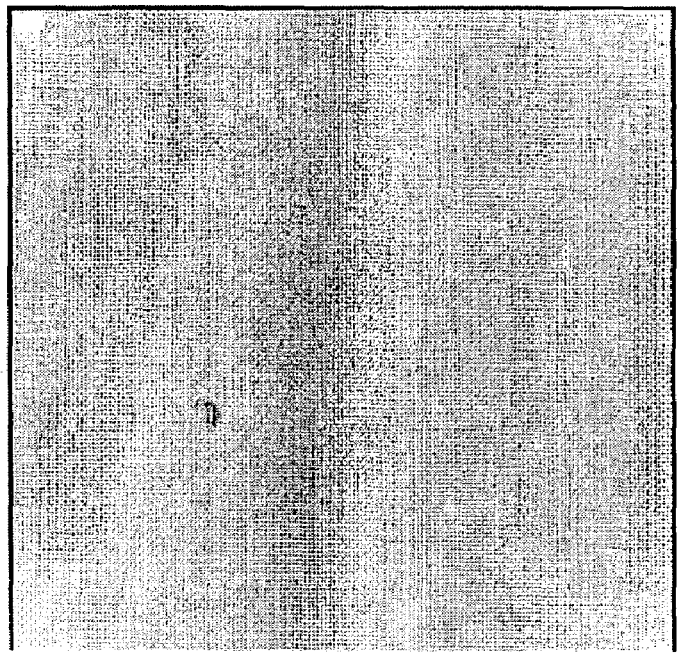
FIGS. 2A and 2B are atomic force microscope (AFM) images of the surface of two classes of gate metal layers.
Figure 2B:
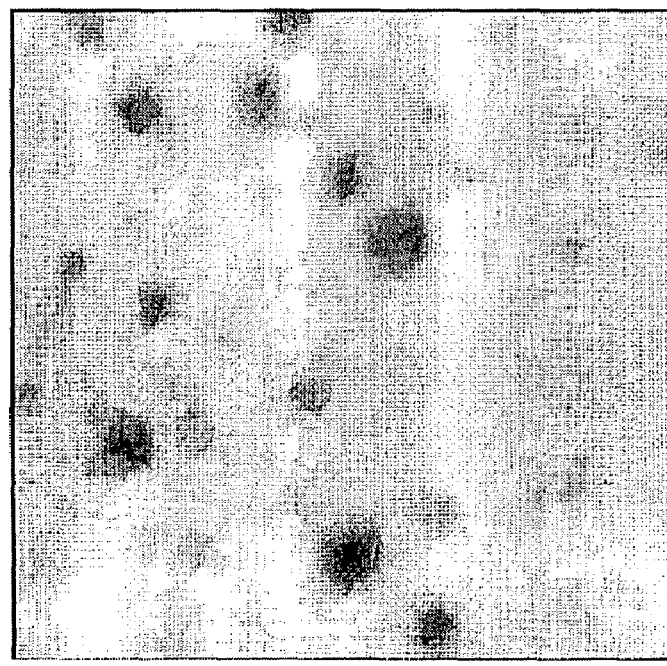

Samples taken from multiple production batches were analyzed by Auger electron spectroscopy depth profiling to verify film composition. A nanoprobe atomic force microscope (AMF) was also used to characterize the top surface of the MIS capacitor. AFM analysis indicated that MIS capacitors with two classes of metal film structures were produced. FIG. 2A is an AMF image of the first type of capacitor, hereafter a Type 1 capacitor, which displays a uniform film morphology. FIG. 2B is an AMF image of a Type 2 capacitor, which displays a non-uniform film morphology. Variations in the surface of the Type 1 capacitors were less than approximately 10 nm. In contrast, the Type 2 capacitors were characterized by large pits in the Pd layer which covered 10-20% of the Pd surface. The pits had a maximum width of approximately 1 μm and the largest of the pits penetrated all the way through to the oxide layer below.

EXAMPLE 2

Flow Cell Testing Conditions and Apparatus

Prior to testing, each capacitor was mounted on a sample holder for insertion into a gas flow cell. Electrical leads were attached to the capacitor base and sensor bonding pads attached to the Pd layer. The resulting sensor was then heated resistively on a conductive pedestal, and the sample temperature was measured by a thermocouple spot-welded to the heater body.

Figure 3:
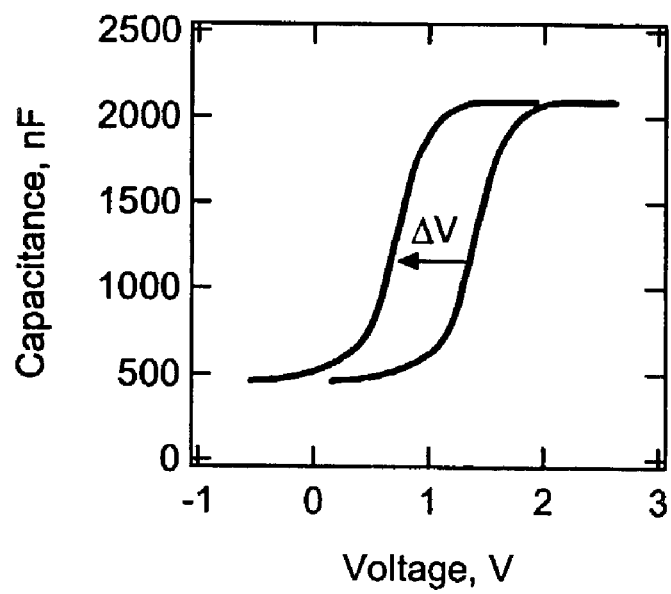
FIG. 3 is a graphical representation of the capacitance-voltage (C-V) curve shift induced by hydrogen exposure to a Pd MIS device.

During flow cell testing, shifts in the C-V curve of the sensor were monitored using a computer-based control algorithm that measured the voltage shift (response) required to maintain a constant capacitance value at a point of maximum slope along the C-V curve. The noise level for measurements made via this method was less than 2 mV. Exposure of the sensor to hydrogen gas caused the C-V curve to shift toward lower bias voltages, as shown in FIG. 3. In order for increasing hydrogen to correspond to increasing signal strength, the sign of the measured response was reversed.

Carbon monoxide, hydrogen, and all other gases were introduced into the flow cell through mass flow controllers. Except as noted otherwise, the pressure in the flow cell was maintained at 50 Torr by means of a vacuum-pumped control valve interfaced with a Baratron pressure gauge. A turbo-pumped mass spectrometer connected to the cell via a vacuum leak valve was used to continuously monitor the concentrations of hydrogen and carbon monoxide in the flow cell. Hydrogen injection studies indicated that the flow cell closely approximated the conditions in a perfectly stirred tank. During testing, the space velocity was approximately 1 $min^{-1}$. All gases were obtained as research-purity from Mattheson Gas Products, East Rutherford, N.J. Argon and/or nitrogen were used as diluents during experimental runs.

Sensors were pretreated under an ambient of 1% hydrogen in helium at 100 Torr and 200° C. for 2 hours prior to flow cell experiments in order to stabilize the response signal.

EXAMPLE 3

Flow Cell Testing: Type 1 Sensors

Figure 4:
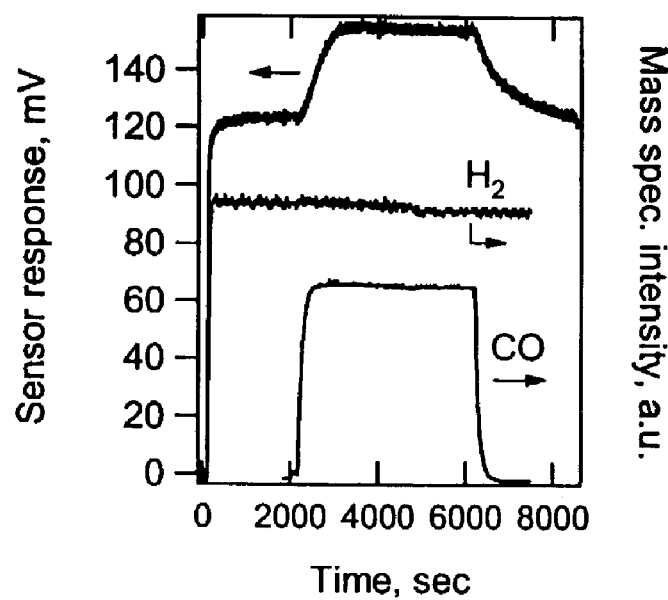
FIG. 4 is a graphical representation of the response of a sensor having a smooth film morphology to sequential $H_2$/CO introduction measured during flow cell experiments at 100° C.; $P_{H2}$=750 mTorr, $P_{CO}$=750 mTorr.

In a series of experiments, the effect of co-fed carbon monoxide on the hydrogen response of Type 1 sensors was examined by the sequential introduction of streams containing hydrogen and carbon monoxide into the flow cell at 100° C.; $P_{H2}$=500 mTorr, $P_{CO}$=500 mTorr. Results from a representative experiment are shown in FIG. 4. A large sensor response was observed almost immediately after addition of hydrogen into the flow cell. This rapid response to hydrogen was typical of all sensors investigated. After allowing the hydrogen response to equilibrate, a stream containing carbon monoxide was introduced into the flow cell. As shown in FIG. 4, the addition of carbon monoxide resulted in a substantial increase in the sensor response signal. The time required for this increase in response varied between different sensors tested and this variation may be attributable to different levels of contamination on the surface of the sensor.

After allowing the carbon monoxide-induced signal to equilibrate, carbon monoxide flow was switched off, resulting in a slow return to the baseline hydrogen response. The observed increase in the sensor response during carbon monoxide exposure was approximately 20% of the baseline hydrogen response. The observed increase is equivalent to a 2-3 decade increase in hydrogen pressure given the broad hydrogen detection range of the sensor. The qualitative behavior illustrated in FIG. 4 was observed for Type 1 sensors over a wide range of experimental conditions ($P_{H2}$=100-2000 mTorr; $P_{CO}$=50-7000 mTorr; and 50-150° C.).

EXAMPLE 4

Flow Cell Testing: Type 2 Sensor High Analyte Partial Pressure

Figure 5A:
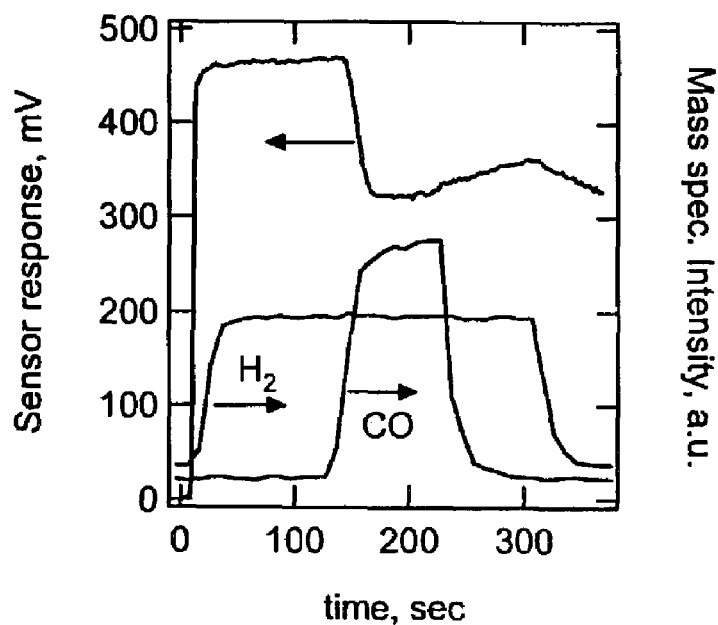
FIGS. 5A and 5B are graphical representation showing the response of a sensor having a non-uniform film morphology at 100° C.

Sensors having non-uniform film morphologies, i.e., Type 2 sensors, were tested at 100° C. via sequential introduction of hydrogen and carbon monoxide at relatively high partial pressures; $P_{H2}$=500 mTorr, $P_{CO}$=850 mTorr. FIG. 5A illustrates the response of a typical experiment. As was seen in the Type 1 sensors, a large sensor response was observed almost immediately after introduction of hydrogen into the flow cell. The sensor response for the Type 2 sensor was, however, noticeably higher than that observed for the Type 1 sensor with a measurable response seen for hydrogen partial pressures of as low as $10^{-6}$ Torr.

After allowing the hydrogen response to achieve its steady-state value, carbon monoxide flow was introduced into the cell. Following an approximately 15 second lag time, the recorded sensor signal decreased over a period of 20 seconds by approximately 120 mV to a constant voltage value. The carbon monoxide was then removed, resulting in a slow recovery toward that observed in the presence of hydrogen alone. Subsequent removal of the hydrogen feed stream led to slow draining of hydrogen from the device. Again, the approximately 33% attenuation in the sensor response during carbon monoxide exposure corresponds to a 4-5 decade drop in hydrogen pressure.

The effect of co-fed carbon monoxide on Type 2 sensors was observed to be in the opposite direction of that for the Type 1 sensors, i.e., carbon monoxide causes a decrease rather than an increase in the measured response.

EXAMPLE 5

Flow Cell Testing: Type 2 Sensors Low Analyte Partial Pressure

Figure 5B:
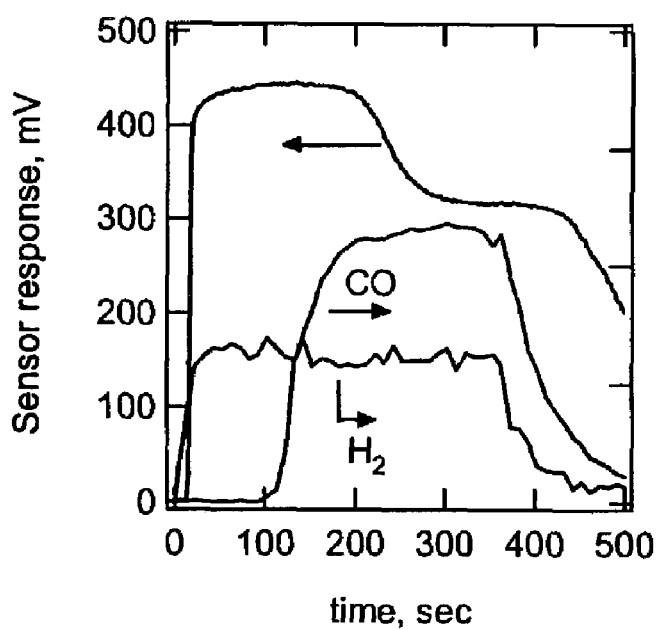

FIG. 5B shows the results of testing on Type 2 sensors using lower analyte partial pressures; $P_{H2}$=75 mTorr, $P_{CO}$=37 mTorr. Sequential introduction of the hydrogen and carbon monoxide again resulted in the same attenuation of the sensor response. Under these conditions however, the lag time for the carbon monoxide induced decrease was approximately 1 minute with a full 2 minutes required for complete onset of attenuation.

EXAMPLE 6

Figure 6:
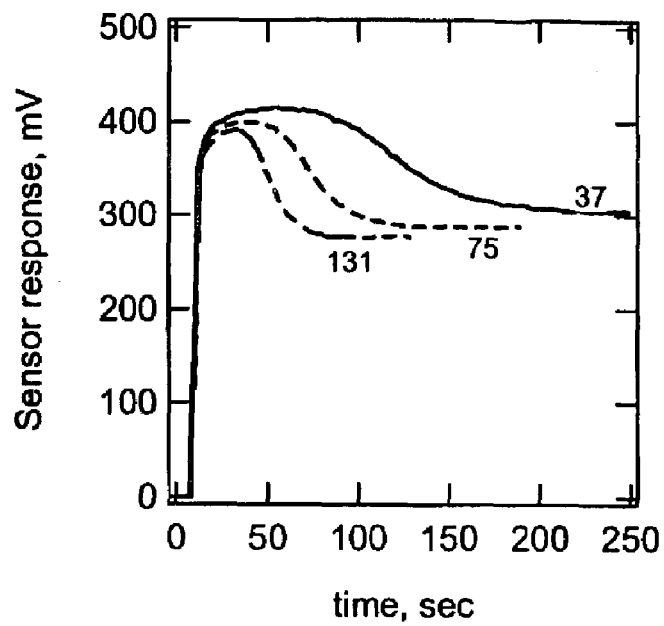
FIG. 6 graphically illustrates the response of a sensor having a non-uniform film morphology to the simultaneous introduction of both $H_2$ and CO for three fuel streams containing CO at different pressures, i.e., $P_{CO}$=37, 75, and 131 mTorr. For each curve, the temperature was 100° C. and $P_{H2}$=75 mTorr.

Flow Cell Testing: Type 2 Sensors Simultaneous Introduction of Hydrogen and Carbon Monoxide As shown in FIG. 6, simultaneous introduction of hydrogen and carbon monoxide at 100° C. also resulted in attenuation of the sensors hydrogen response. In three separate experiments, various pressures of carbon monoxide, 37 mTorr, 75 mTorr, and 131 mTorr, were co-introduced with hydrogen at a partial pressure of 75 mTorr. For all carbon monoxide pressures, the sensor response initially increased and reached a maximum value, indicating the presence of hydrogen. Then, after a certain amount of lag time, the sensor response gradually decreased to a constant steady-state value. As shown in FIG. 5, the rate of the carbon monoxide-induced attenuation was strongly dependent on the carbon monoxide partial pressure.

EXAMPLE 7

Flow Cell Testing: Type 2 Sensors Percent Attenuation Studies

Figure 7:
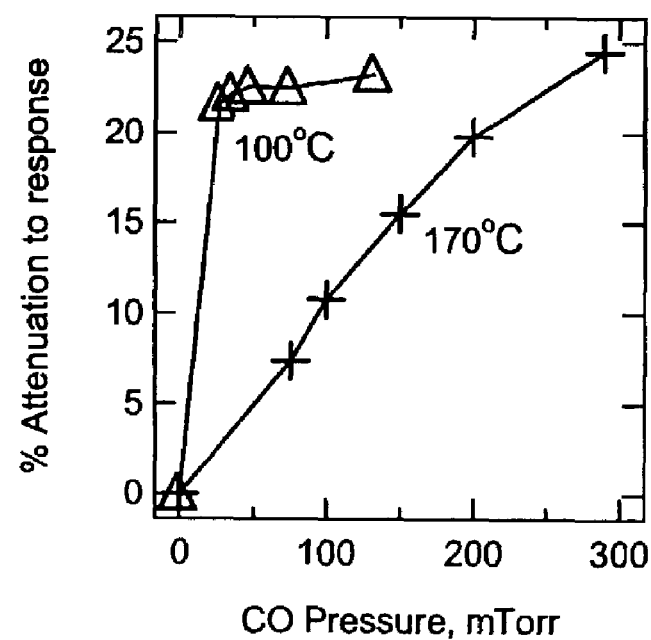
FIG. 7 graphically depicts the percent attenuation in a steady-state $H_2$ response of a sensor having a non-uniform film morphology as a function of CO partial pressure. The result are indicated for two temperatures, 100° C. and 170° C., with $P_{H2}$=75 mTorr.

FIG. 7 graphically depicts the percent attenuation in a steady-state hydrogen response of a Type 2 sensor as a function of CO partial pressure. The experiment was conducted at two temperatures, 100° C. and 170° C., with $P_{H2}$=75 mTorr. As indicated in FIG. 7, the sensor response remained approximately constant over a wide range of carbon monoxide pressures, suggesting that complete saturation of the attenuation effect may be achieved with partial pressures of carbon monoxide as low as 50 mTorr.

The linearity of the attenuation effect at 170° C. is consistent with the expectation that at higher temperatures the surface coverage of carbon monoxide for a given gas phase will be decreased. This is due to an increase in the rate constant for carbon monoxide desorption. The carbon monoxide pressure required for saturation will therefore be higher at higher temperatures, resulting in a sensor response that is a more linear function of carbon monoxide above 50 mTorr.

We claim:

1. A carbon monoxide sensor for use in a hydrogen feed stream, comprising:
   a metal/insulator/semiconductor (MIS) structure capable of generating electrical signals in response to hydrogen and carbon monoxide, comprising:
   a semiconductive substrate;
   an insulating inorganic oxide layer on the semiconductive substrate, wherein said insulating inorganic oxide layer comprises a thinned region;
   a metal layer deposited onto the thinned region of the insulating inorganic oxide layer thereby forming a gate metal layer;
   a first conductor means connected to the gate metal layer;
   a second conductor means connected to the semiconductive substrate; and
   signal processing means in electrical communication with the first and second conductor means for processing the electrical signals to determine if carbon monoxide is present in the hydrogen feed stream.

2. The carbon monoxide sensor of claim 1, wherein the metal layer is selected from the group consisting of palladium and palladium alloys.

3. The carbon monoxide sensor of claim 2, wherein the gate metal layer is approximately 20 nm to approximately 500 nm in thickness.

4. The sensor of claim 3, wherein the gate metal layer is approximately 20 nm to approximately 200 nm in thickness.

5. The sensor of claim 2, wherein the gate metal layer has a uniform film morphology.

6. The sensor of claim 2, wherein the gate metal layer has a non-uniform film morphology.

7. The carbon monoxide sensor of claim 6, wherein the non-uniform film morphology comprises variations in the thickness of the gate metal layer that are greater than approximately 10 nm.

8. The carbon monoxide sensor of claim 6, wherein the non-uniform film morphology takes the form of a plurality of pits or cavities in the gate metal layer that may optionally expose the insulating inorganic oxide layer.

9. The carbon monoxide sensor of claim 8, wherein the pits or cavities cover approximately 1% to approximately 30% of the gate metal layer.

10. The carbon monoxide sensor of claim 2, wherein the gate metal layer is comprised of palladium.

11. The carbon monoxide sensor of claim 2, wherein the gate metal layer is comprised of a palladium alloy.

12. The carbon monoxide sensor of claim 11, wherein the palladium alloy comprises a material selected from the group consisting of silver, gold, copper, nickel, and platinum.

13. The carbon monoxide sensor of claim 2, further comprising a selectively permeable membrane on the gate metal layer.

14. The sensor of claim 13, wherein the selectively permeable membrane is comprised of inorganic material.

15. The sensor of claim 14, where in the inorganic material comprises a zeolite.

16. A method for determining the presence of carbon monoxide in a hydrogen feed stream of interest, comprising the steps of:
   a. providing the carbon monoxide sensor comprising:
      1. a semiconductive substrate;
      2. an insulating inorganic oxide layer on the semiconductive substrate, wherein said insulating inorganic oxide layer comprises a thinned region;
      3. a metal layer deposited onto the thinned region of the insulating inorganic oxide layer thereby forming a gate metal layer;
      4. a first conductor means connected to the gate metal layer;
      5. a second conductor means connected to the semiconductive substrate; and
      6. signal processing means in electrical communication with the first and second conductor means for processing the electrical signals to determine if carbon monoxide is present in the hydrogen feed stream;
   b. providing a calibration signal;
   c. exposing the sensor to the hydrogen feed stream of interest and recording the electrical signals generated thereby; and
   d. determining the presence of carbon monoxide by comparing the calibration signal to the signal generated when the sensor was exposed to the hydrogen feed stream of interest.

17. The method of claim 16, wherein the step of providing a carbon monoxide sensor further comprises:
   providing a metal layer selected from the group consisting of palladium and palladium alloys.

18. The method of claim 17, wherein the gate metal layer has a uniform film morphology.

19. The method of claim 18, wherein the calibration signal is greater than the signal generated when carbon monoxide is present.

20. The method of claim 17, wherein the gate metal layer has a non-uniform film morphology.

21. The method of claim 20, wherein the calibration signal is greater than the signal generated when carbon monoxide is present.

22. The method of claim 21, wherein steps b and c are performed simultaneously and the calibration signal is derived from the electrical signals generated during the first 10 seconds of the exposure of the sensor to the hydrogen feed stream of interest.

23. The method of claim 16, wherein the method is capable of detecting carbon monoxide at concentrations ranging from approximately 0.05 ppm to approximately 1000 ppm at atmospheric pressure.

24. The method of claim 16, wherein the method is carried out at a temperature ranging from approximately 80° C. to approximately 250° C.

25. The method of claim 19, wherein the electrical signals generated during step c are indicative of an approximately 2 to approximately 3 decade increase in the amount of hydrogen present in the feed stream.

26. The method of claim 21, wherein the electrical signals generated during step c are indicative of an approximately 4 to approximately 5 decade decrease in the amount of hydrogen present in the feed stream.

* * * * *